United States Patent [19]
Olsen

[11] Patent Number: 5,160,828
[45] Date of Patent: Nov. 3, 1992

[54] ELECTROMAGNETIC WARMING OF SUBMERGED EXTREMITIES

[75] Inventor: Richard G. Olsen, Pensacola, Fla.

[73] Assignee: The United States of America as represented by the Secretary of the Navy, Washington, D.C.

[21] Appl. No.: 489,161

[22] Filed: Mar. 6, 1990

[51] Int. Cl.$^5$ ............................................. H05B 1/00
[52] U.S. Cl. ................... 219/211; 219/529; 219/549; 128/422; 128/379
[58] Field of Search ............... 219/211, 212, 522, 527, 219/528, 529, 549, 10.55 R, 10.55 A, 10.55 M, 10.79; 2/2.1 A, 2.1 R; 128/422, 402, 379, 381, 382, 383

[56] References Cited

U.S. PATENT DOCUMENTS

| | | | |
|---|---|---|---|
| 2,858,410 | 10/1958 | Rich | 219/211 |
| 3,497,672 | 2/1970 | Harter et al. | 219/211 |
| 3,501,616 | 3/1970 | Arron | 219/211 |
| 3,621,191 | 11/1971 | Cornwell | 219/211 |
| 3,657,515 | 4/1972 | Smith | 219/211 |
| 4,671,286 | 6/1987 | Renault | 128/422 |
| 4,679,561 | 7/1987 | Doss | 128/422 |
| 5,008,517 | 4/1991 | Brekkestran et al. | 219/211 |

Primary Examiner—Bruce A. Reynolds
Assistant Examiner—Tu Hoang
Attorney, Agent, or Firm—A. David Spevack; William C. Garvert

[57] ABSTRACT

The invention is a device encompassing and warming the extremity of a worker in a cold wet environment. The device can take the form of a glove, sock and/or arm and/or leg warmer. The device contains a coil surrounding the extremity. The coil forms an envelope surrounding each extremity and each digit of an extremity. A water free, RF transmitting zone encompasses the coil envelope. The coil, extremity and RF transmitting zone combine to provide a resonant frequency with the operating frequency with which the coil is driven. The combination warms the interior of the extremity. The RF energy is provided from a source carried at some other point on the subjects body. The entire combination on each extremity and the power source can be encompassed in a shield layer which absorbs or reflects RF energy into the extremity.

9 Claims, 5 Drawing Sheets

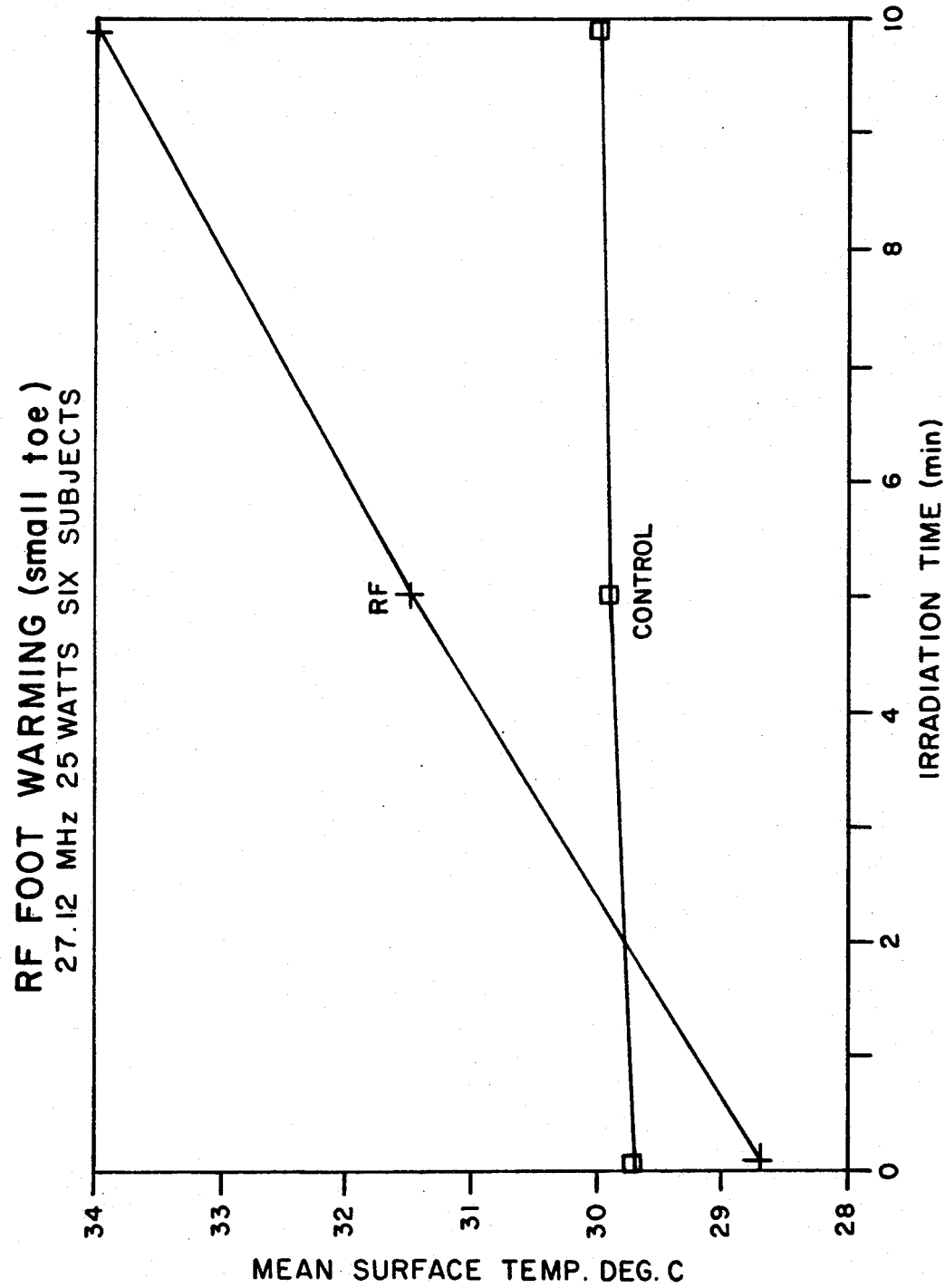

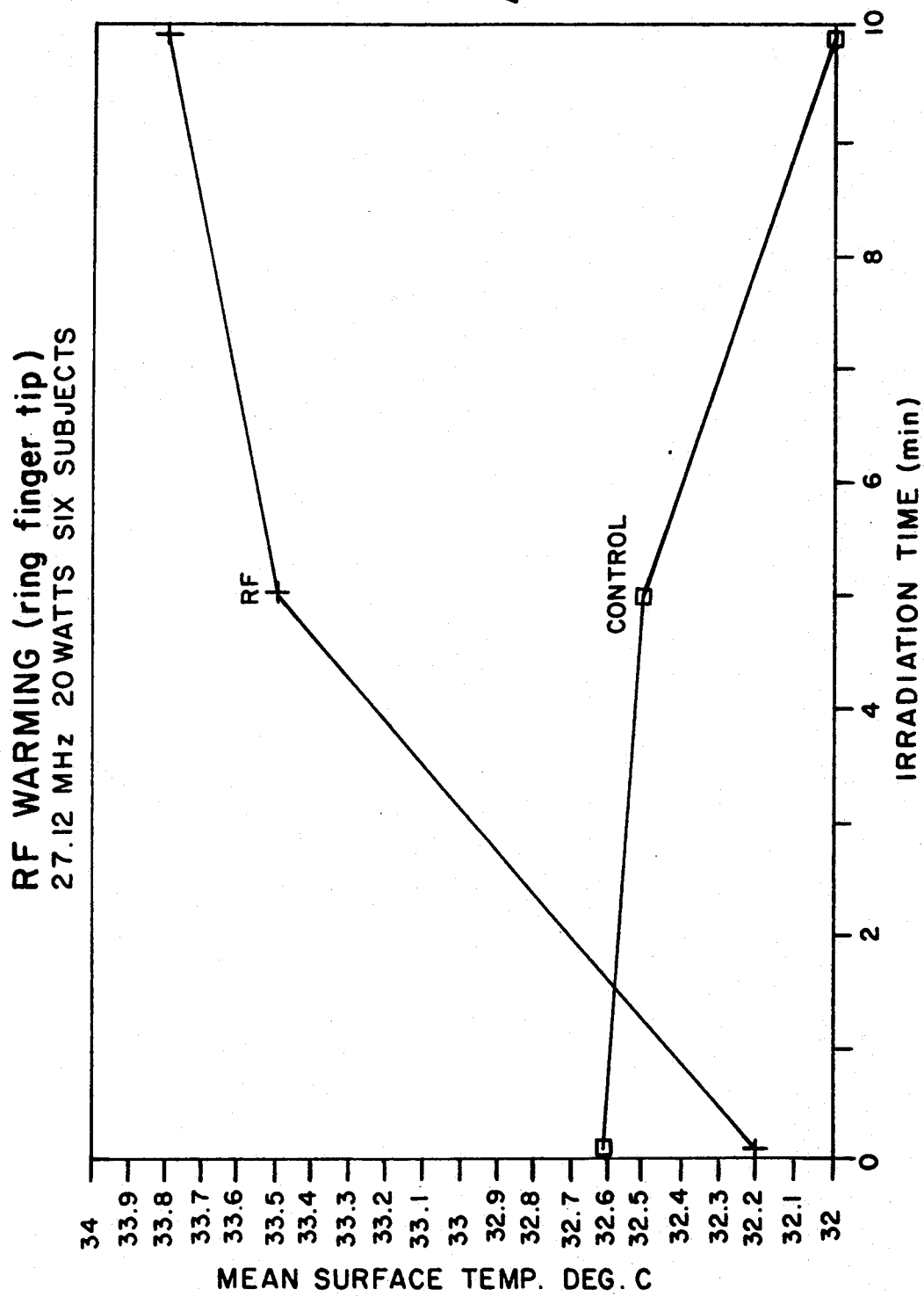

ELECTROMAGNETIC WARMING OF SUBMERGED EXTREMITIES

BACKGROUND OF THE INVENTION

1. Field of the Invention

This invention relates to devices for preventing cold induced reductions in the dexterity of the extremities of divers and others working in wet or submerged conditions. More particularly, this invention relates to boots, sleeves, leggings and gloves which can heat or maintain at a level temperature the total volume of a persons extremities using radio frequency (RF) energy.

2. Description of the Prior Art

It has been well documented that the environmental factor of cold water is a prime cause of impaired diver performance (Bachrach et al., "Human Performance Underwater", Dividing Medicine (R. H. Strauss, ed.), pp. 183-196, Grune et al., New York (1976); Curley et al., "Wet-suited Scuba Diver Performance in 5°-25° C. Water", Report NMRI 81-51, Naval Medical Research Institute, Bethesda, Md. (1981)). A reduction or loss of a persons dexterity typically occurs at finger temperatures below about 15° C. (Clark, "The Limiting Hand Skin Temperature For Unaffected Manual Performance In The Cold", J. Appl. Physiol. 45, pp. 193-194 (1961); Dusek, "Effect of Temperature on Manual Performance", Protection and Function of the Hands in Cold Climates, F. R. Fisher, ed., pp. 63-76, National Academy of Sciences, Washington, D.C. (1957)). Purely passive thermal hand protection is self defeating because it necessitates the use of bulky gloves or mittens and precludes the full usefulness of the hands.

To date, active thermal protection of the extremities has involved surface-applied heat such as warm water or direct electrical current to heat a resistive wire. Surface-applied heating methods tend to be inefficient in cold water because of large conductive heat losses and because of the thermal limitations caused by skin burning. Radio frequency (RF) energy has received little attention for use in extremity warming even though the deep-heating properties of helical RF coils for tumor therapy and hypothermia resuscitation have been demonstrated (Olsen, "Reduced Temperature Afterdrop in Rhesus Monkeys With Radio Frequency Rewarming", Aviat. Space Environ. Med., 59, pp. 78-80 (1988); Olsen et al., "Hypothermia and Electromagnetic Rewarming in the Rhesus Monkey", Aviat. Space Environ., 55, pp. 1111-1117 (1984); Ruggera et al., "Development of a Family of RF Helical Coil Applicators Which Produce Transversely Uniform Axially Distributed Heating in Cylindrical Fat-muscle Phantoms", IEEE Trans. Biomed. Eng., BME-31, 98-106.5-7 (1984)).

Systems exist, such as hunting socks, which provide heat to the skin surface by means of a DC current flowing through resistive wire. These surface heaters are inefficient often requiring bulky, high energy power sources. In addition, surface heaters can cause surface burns if the temperature is raised sufficiently to warm the extremity core. A system that deposits energy within the volume of an extremity rather than at its surface is more efficient in maintaining a diver's manual dexterity without the need for a prohibitively large and bulky electrical power source.

In U.S. Pat. No. 4,685,462, the inventor herein, R. G. Olsen, describes a jacket-type device which utilizes a torso-encircling resonant coil irradiation system to resuscitate hypothermic subjects. The torso device was found to operate successfully in an air environment. Water between the windings of the coil was found to interfere with operations. There was a need for an active warming device which is operable under submerged or near submerged conditions.

SUMMARY OF THE INVENTION

Accordingly, an object of this invention is an active means for maintaining the extremities of a person operating in wet, cold environments warm and flexible.

Another object of this invention is a means of preventing loss of dexterity in the extremities of divers operating in cold water.

A further object of this invention is a means of utilizing RF energy to prevent the loss of dexterity in the extremities of divers and others working in cold wet environments.

Yet an additional object of this invention is an active device for warming extremities of divers operating in cold water which provides an RF wave conduction zone free of water.

Also, an object of this invention is a device utilizing a low energy power source while actively providing warmth to the extremities of a person operating in a cold, wet environment.

These and additional objects of the invention are accomplished by a device encompassing the extremity. The device can take the form of a glove, sock and/or arm and/or leg warmer. The device contains a coil surrounding the extremity. The coil forms an envelope surrounding each extremity an each digit of an extremity. A water free, RF transmitting zone encompasses the coil envelope. The coil, extremity and RF transmitting zone combine to provide a resonant frequency with the operating frequency with which the coil is driven. The combination warms the interior of the extremity. The RF energy is provided from a source carried at some other point on the subjects body. The entire combination on each extremity and the power source can be encompassed in a shield layer which absorbs or reflects RF energy into the extremity.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

FIG. 1a is an enlargement of a sock embodiment of the invention.

FIG. 1b is a representation of the power source and one embodiment of its placement.

FIG. 1c is a an enlargement of a glove embodiment of the invention.

FIG. 5 is a graph of results of the use of the invention in warming a foot.

FIG. 6 is a graph of results of the use of the invention in warming a finger.

DESCRIPTION OF THE PREFERRED EMBODIMENTS

The device of this invention in its different embodiments is a means of maintaining the extremities, including digits on the extremities, warm. The device is an active means actually producing extremity warming as opposed to passive means such as insulating gloves. In its most useful embodiment, the invention is used by divers to provide warmth to extremities when working in cold water.

Water is an excellent heat sink and can rapidly absorb heat from an exposed heat generator such as the human body. Insulating materials only reduce heat conduction away from the heat generator. Insulators do not stop heat conduction altogether. The colder the water the greater the quantity of heat conducted away. The body is a limited heat generator. When the amount of heat conducted away from the diver's body, even through insulating garments, exceeds the heat generated by the body, the diver will get cold and lose mobility and flexibility. As is well known to anyone living in a cold clime, the extremities, particularly the digits, are the first to get cold enough to lose flexibility. To maintain flexibility, it is necessary to provide heat to the extremity.

Figure 1:
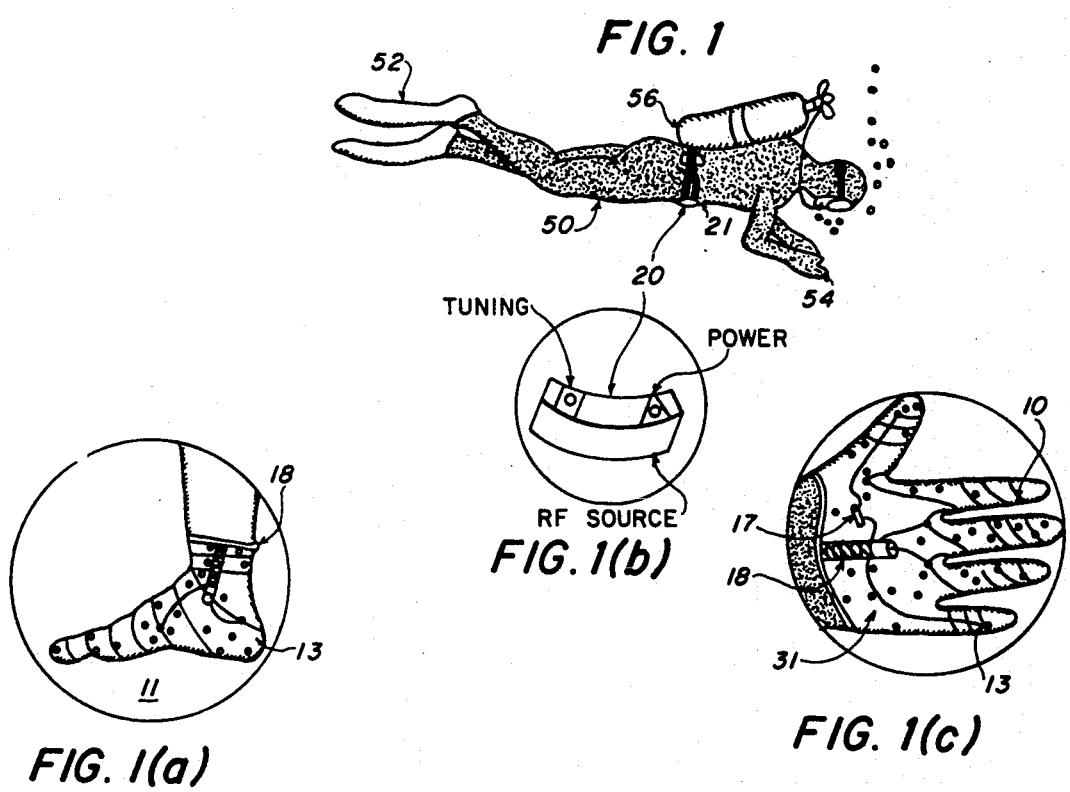
FIG. 1 is a sketch of two embodiments of the device and placement of the power source on a scuba diver.

In the embodiment illustrated in FIG. 1, a scuba diver 50 wears a wet suit 56 having boots 16 within flippers 52 and gloves 54. A power source 20 is carried in a convenient place on the divers body such as part of the belt 21. The power source 20 is connected through a cable 18 to each warming unit on each extremity. The power source can be a radio frequency oscillator/amplifier circuit powered by a battery pack such as subassemblies from ENI Inc., Model ACG-3-27 RF source powered by batteries totaling about 40 V.

The invention is a coil envelope formed of wrap of wire also known as turns, pitches, windings, etc. ostensibly helical for the forearm and foot, and somewhat modified for the hand. The coil wraps are wound over the skin using common insulated 18-30 AWG hook-up wire. In the most convenient form the coil wraps are wound and affixed to a glove structure 31 or sleeve or sock 13. This sleeve, sock or glove facilitates the rapid donning of the coil structure. For convenience the glove, sock or sleeve structures are referred to generically as "foundation sleeve".

Figure 2:
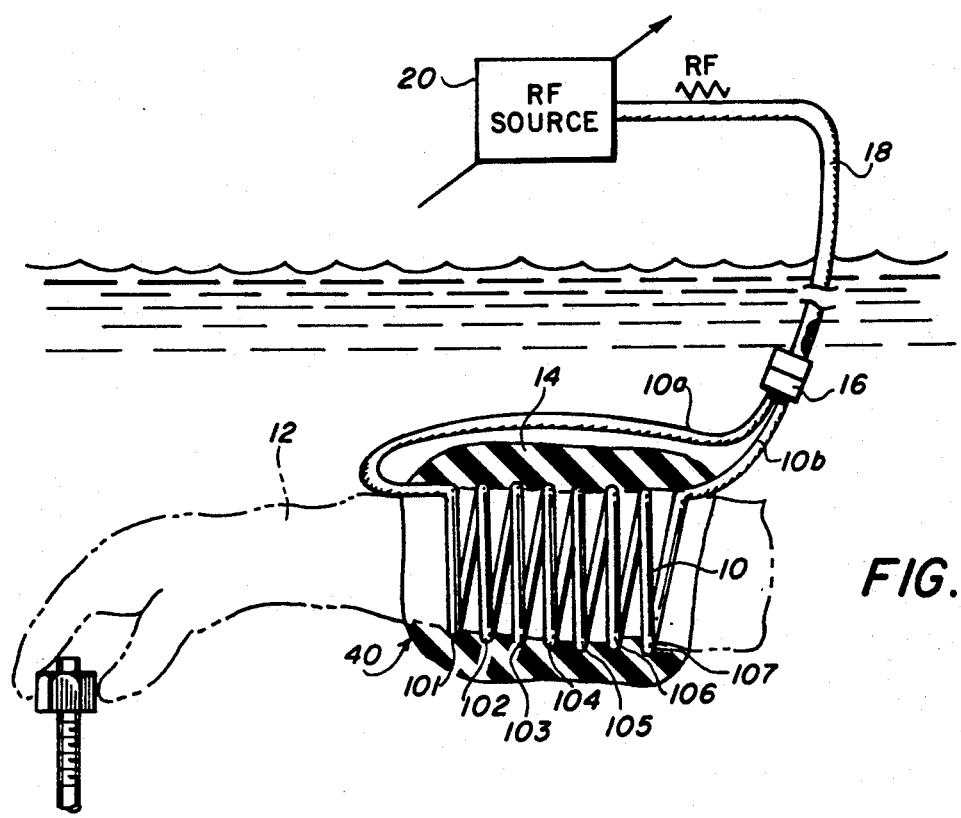
FIG. 2 is a detail cross sectional view of an arm warmer embodiment of the invention.

It was found that to operate successfully in a wet or underwater environment, it was necessary to prevent water from interposing itself between the coil wraps by providing an RF transmitting zone. In FIG. 2, the RF transmitting zone 14 is formed of a material which insures a water free, RF transmitting zone between the coils 101 through 107 of the wire 10. A water free zone does not mean that each wire turn should be water proof and dry, which of course it must be for electrical reasons. A water free zone means that the "line of site between each coil wrap must be free of water or any other RF absorbing material.

The RF transmitting zone, such as 14, is formed of an RF transmitting material which will exclude water or other RF absorbers or reflectors from the space between the coil wrap. In the simplest form, the zone 14 can be formed from layers of petroleum jelly impregnated cloth wrapped around the coil envelope formed by wire 10. The zone can be formed from any suitable water-displacing material that will provide an RF transmitting zone for fluctuating electromagnetic fields around the coils. Of course, an RF transmitting zone should be non-conducting in the electrical sense (a dielectric material). In the foot embodiment of FIG. 3, the zone 14 can take the form of a sock made of water impervious material which has sufficient thickness that an RF transmitting zone is left between the coil wrap after the sock 14 has conformed to the height of the coil wrap formed by the wire 10. Polymeric materials are preferred. Most preferred are those materials which form artificial fibers and non-woven materials. Wetable materials, such as cotton or wool can be used as the RF transmitting zone if the material is sealed to prevent water from entering the structure of the fabric. To be useful in this invention, it is not necessary for the material of the RF transmitting zone itself to be impervious to water. The techniques for rendering materials water impervious or the lists of water impervious materials are well known.

Referring to FIG. 2, forearm warmth is provided by a helical coil formed by wire 10. The wire forming the coil envelope 10 can be wound directly about the forearm 12 of a diver or, more preferably, the coil is attached to an inner liner shaped to conform to the body part to be warmed. An RF transmitting zone 14 is formed around the coil wrap 10. In its preferred form, the RF transmitting zone is formed from a water impervious light weight and flexible material which will conform to the coils and keep water or other RF reflecting or absorbing materials from interposing between the coil wrap. Wire leads 10a and 10b connect the ends of the coil through a suitable waterproof connection 16 to a cable 18 which, in turn, is connected to a source of RF energy 20 having variable frequency capability and adjustable output power.

The RF source 20 provides energy at the resonant frequency of the coil/extremity/transmitting zone combination when immersed in water. Of course, wet or dry diving suits may be worn over the combination.

Figure 3:
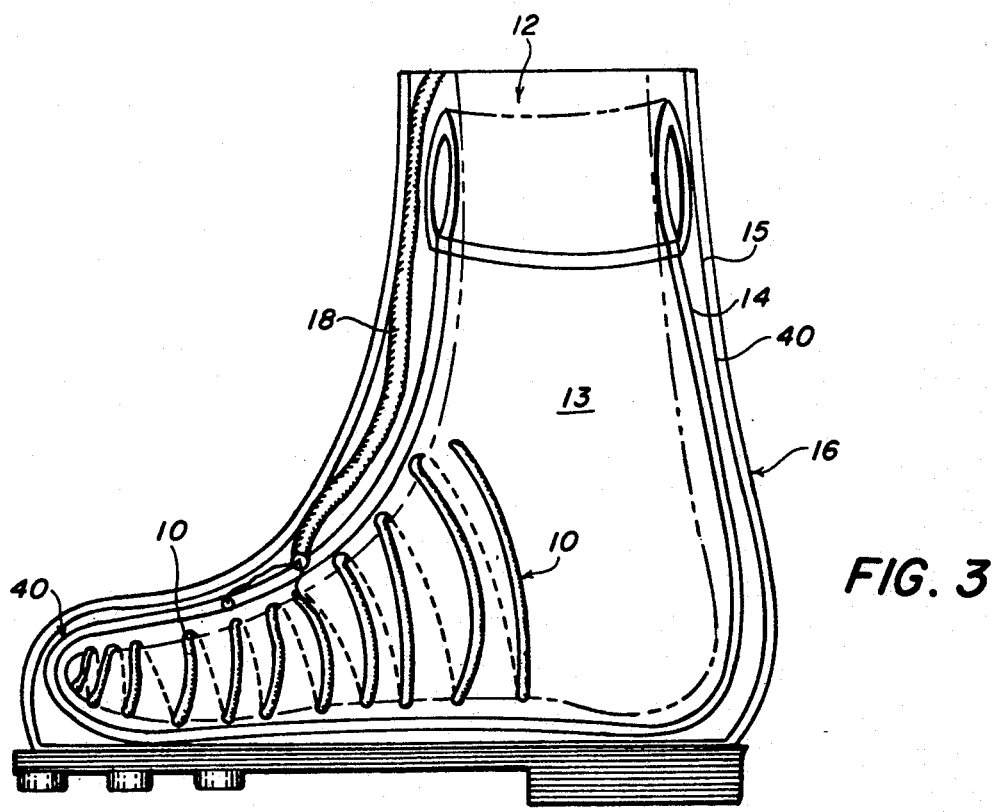
FIG. 3 is a detail cross sectional view of a boot or sock embodiment of the invention.

Referring to FIG. 3, foot warmth is provided by the helical coil 10 wound about the foot 12 including the toes. In most instances the toes will not be treated individually, as are the fingers, but they can be as needed. In this embodiment, the RF transmitting zone comprises a thermal insulating sock 14 in combination with the divers boot 16. In this case the sock 14 can be wet but the boot 16 prevents wetting and retains the necessary RF absorber reflector free atmosphere. A small coaxial cable 18 delivers the RF energy and connects the coil 10 through the sock. The cable is routed through the inside of the suit for exit at some convenient location. In the preferred embodiment, as illustrated in FIG. 1a and FIG. 3, the coil is mounted on a liner 13 in the form of a sock. The RF transmitting zone can be permanently formed over the coil 10 to form an easily donned assembly 11.

Figure 4:
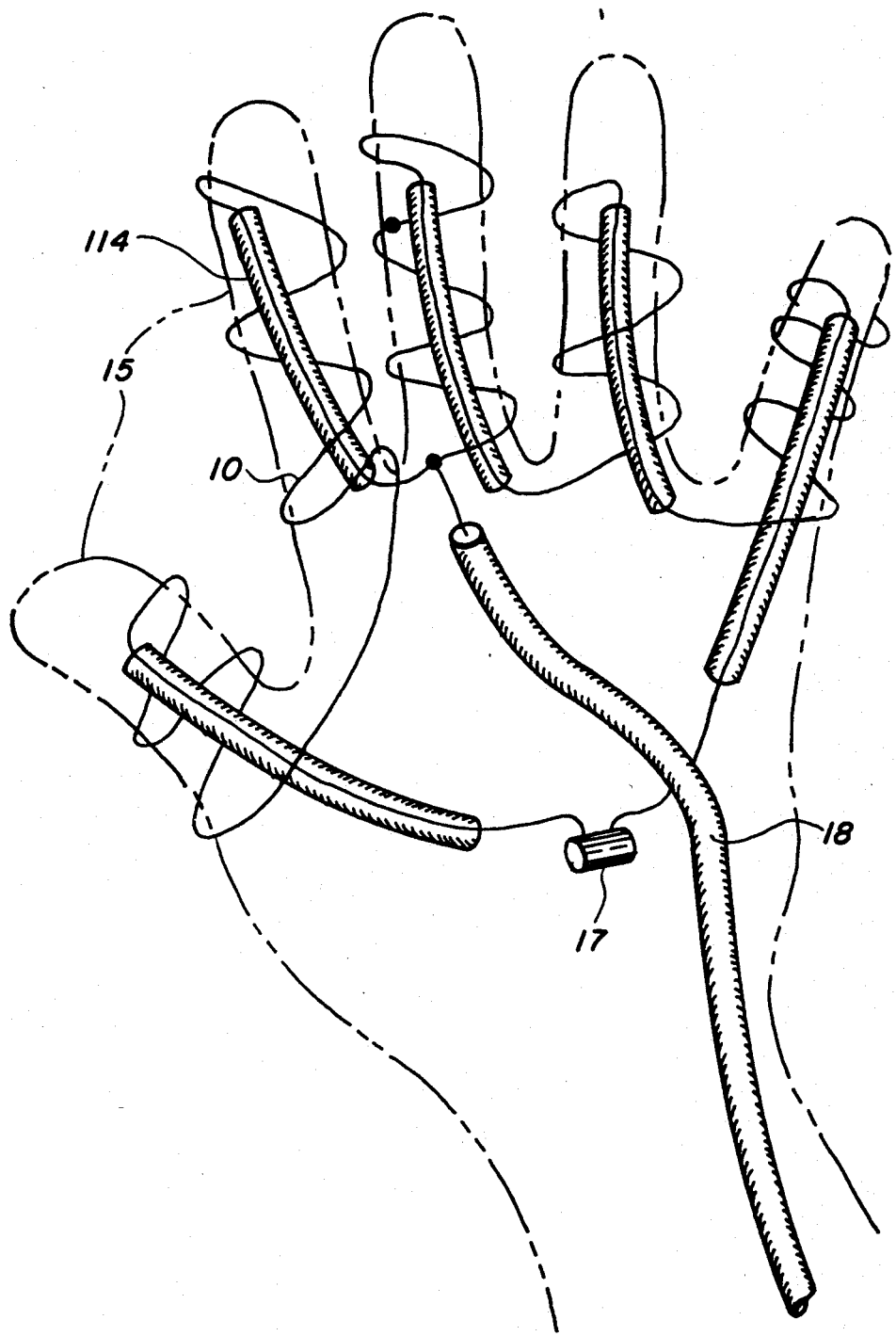
FIG. 4 is a detail view of the coil envelope of a glove embodiment of the invention.

Referring to FIG. 4 and FIG. 1c, hand warmth is provided by a helical coil envelope 10 wound serially over the fingers 15. Spacers 114 provide clearance of at least several wire diameters in places where the coil crosses over itself. This avoids internal localized interactions of the RF signal. In the foot, arm and leg embodiments crossover problems are avoid by running the wire above and below the RF transmitting zone or by other techniques to avoid "shorting" the coil envelope.

The spacers 114 can take the form of plastic tubing or other insulating and spacing material including cloth, plastics, paper and the like. The ends of the coil 10 are connected at a central location on the back of the hand and connected to a 3-50 pf variable capacitor 17. A coaxial coil 18 delivers RF energy directly to the coil 10. It is preferred that the coil and all parts be attached to a liner 13 in the form of a glove. The RF transmitting zone can be the divers glove 54 or, more preferably, a zone formed permanently over the coil. The RF hand coil assembly 10 was fashioned as a series connection of finger coils from 1.8 m of solid, 18 AWG insulated copper hook-up wire. The coil 10 was wound over a (right hand) cotton work glove to facilitate repeated use by multiple subjects. Radio frequency energy at 27.12 MHz, an industrial, scientific, and medical (ISM) channel, was fed to the central portion of the hand coil through a length of RG/58A coaxial cable 18 and a 1-ampere, type 3AG fuse. A banana plug and jack formed the other electrical connection, and insulating tape covered all bare conductors. In actual use, adjustment to a 50-ohm impedance match at 27.12 MHz was made with the aid of a network analyzer. Small subject-to-subject offsets in resonant frequency were accommodated by adjusting the variable capacitor to permit operation entirely at 27.12 MHz.

The RF signal generated by the coil will broadcast from the wearers extremities. This signal may interfere with devices and equipment being handled by the diver. The signal may also disclose the divers location if it can be detected at great distances. It is therefore preferred to extend an RF energy absorbing or reflecting layer, illustrated as 40 in FIGS. 2 and 3, over the RF transmitting zone encompassing the entire RF transmitting zone and preventing the escape of at least the major portion of the RF energy back into the extremity. The layer 40 can take the form of a metal foil, carbon impregnated cloth or the like.

In tests, a 12-channel, optical fiber thermometry system (Clinitherm model T-1200) was used to determine temperatures of the hand. Before donning the glove-mounted hand coil assembly, ten temperature probes were attached to the subject's right hand, two each on the palm side of each finger (ball of fingertip opposite the nail and fleshy region between the two most distal joints). Two additional probes were placed on the top and bottom of the central palmar region. Temperature probe output was printed at 30-second intervals during each experiment.

A four-channel optical fiber thermometry system (Luxtron model 750) was used in the foot warming experiments. Before the subject placed his foot in the nylon sock 13, a temperature probe was taped in place on the bottom of the big toe, on bottom of the little toe, on the top of the foot under the central portion of the coil, and on the bottom of the foot at the instep. As in the hand warming experiments, temperature probe output was printed at 30-second intervals.

The RF System for tests is a 50-watt military radio transmitter (AN/WRC-1) generating and amplify a 27.12 MHz RF signal. A Bird model 43 in-line power meter was used to monitor net RF power applied to the coils.

For the hand-and foot-warming experiments, both control and irradiation experiments were conducted with each subject serving as his own control. Control experiments were identical to those involving RF irradiation except that the RF generating apparatus was not energized. Hand-warming experiments used 20 W net RF power, and foot-warming experiments used 25 W. These power levels were selected as being comfortable for all subjects and less than the average, whole-body specific absorption rate (SAR) allowed by ANSI C95.1-1982. After the coil assembly had been secured to either the right hand or the right foot, two polyethylene bags were placed over the extremity before it was immersed into a 15-gallon plastic tub containing simulated sea water, a three percent (by weight) salt solution at room temperature ($24°\pm2°$ C. The rectangular plastic bags were sufficiently long to encase the submerged limb within a protective dam; thereby, excluding the simulated sea water from intimate contact with the coil assembly. In the foot-warming experiments, three layers of elastic bandages were wrapped over the coil assembly to simulate the insulating effect of a heavy sock and dry boot. No bandages were used over the hand coil to simulate the limited insulating effect of a lightweight work glove. After immersion, data acquisition from the thermometry system was started. A 15-minute equilibration period was then commenced followed by a 10-minute irradiation (RF experiments only) which was followed by a five-minute post irradiation period for a total immersion time of 30 minutes.

DATA ANALYSIS. For the 10-minute period of RF irradiation, experimental and control temperatures were statistically compared at two-minute intervals beginning with the start of irradiation. For each subject and probe location, a normalized temperature increment (DELTA T) was obtained by subtracting the "irradiation" temperature from the "control" temperature and further subtracting any initial temperature offset such that at zero irradiation time, the normalized temperature increment (DELTA T) was zero. The resulting distributions of normalized RF-induced thermal rises were analyzed using a repeated measures analysis of variance (ANOVA) and tested at the $p=0.05$ level of significance for any change over time.

The tests show that when the coil is driven at its resonant frequency, typically in the range of about 10 MHz to about 50 MHz at a power level of about 10 to 50 watts, the internal heating of the forearm, foot, and hand serves to greatly reduce the decrease in manual dexterity and discomfort in the extremities that are otherwise experienced in cold water. FIG. 5 shows a comparison of heating in the submerged small toe of six human subjects who were fitted with a coil energized at 27.12 MHz with 25 watts. The water temperature was approximately 21° C. FIG. 6 shows a similar comparison of finger warming in six subjects who were fitted with a coil energized at 27.12 MHz with 20 watts. The water temperature was about 21° C.

Manual dexterity tests in cold water using a standardized task such as unscrewing nuts from one set of studs and threading them onto another with varying levels of power applied to a forearm coil similar to that illustrated in FIG. 2, shows the effectiveness of RF heating of the forearm. Exclusion of water from a zone outside the outer envelope of the coil avoids the disruption of the electromagnetic field and lack of effective tissue heating in extremities that occurs when water, particularly salt water, intrudes between the coil wrap per se.

The coil and RF transmitting zone may be incorporated into diving gear in many forms such as built into sleeves and leggings, gloves, gauntlets and the like. Obviously, many modifications and variations of the present invention are possible in light of the above teachings. It is therefore to be understood that, within the scope of the appended claims, the invention may be practiced otherwise than as specifically described.

What is claimed is:

1. A device for preventing cold induced reductions in the dexterity of extremities comprising:
   a coil of several wraps forming an envelope surrounding an extremity;
   a water excluding, RF transmitting zone formed of at least one layer of dielectric material substantially free of RF absorbing and reflecting material encompassing the coil envelope and occupying all space between the wraps of the coil;
   a variable RF source generating RF energy to drive the envelope coil at a pre-selected frequency, the combination of coil, extremity, and RF transmitting zone resonant at a frequency at which the coil is driven.

2. A device according to claim 1 wherein the coil is mounted on a support structure.

3. A device according to claim 2 wherein the support structure is in the form of a glove.

4. A device according to claim 2 wherein the support structure is in the form of a sock.

5. A device according to claim 2 wherein the support structure is in the form of a tue encompassing an arm or leg.

6. A device according to claim 1 wherein a layer of material capable of reflecting RF energy encompasses the RF transmitting zone to prevent the escape of at least a major portion of the RF energy from the extremity selected from the group of material capable of reflecting RF energy and material capable of absorbing RF energy encompasses the RF transmitting zone.

7. A device according to claim 6 wherein the device is in the form of a glove.

8. A device according to claim 6 wherein the device is in the form of a sock.

9. A device according to claim 6 wherein the device is in the form of a tube capable of encompassing an arm or leg.

* * * * *